United States Patent
Rasmussen

(10) Patent No.: US 11,684,310 B2
(45) Date of Patent: *Jun. 27, 2023

(54) DEVICES AND METHODS FOR NERVE MAPPING

(71) Applicant: J3G Spine, LLC, Austin, TX (US)

(72) Inventor: Jann Rasmussen, Leander, TX (US)

(73) Assignee: J3G Spine, LLC, Austin, TX (US)

( * ) Notice: Subject to any disclaimer, the term of this patent is extended or adjusted under 35 U.S.C. 154(b) by 568 days.

This patent is subject to a terminal disclaimer.

(21) Appl. No.: 16/854,991

(22) Filed: Apr. 22, 2020

(65) Prior Publication Data

US 2020/0261021 A1   Aug. 20, 2020

Related U.S. Application Data

(63) Continuation of application No. 15/685,960, filed on Aug. 24, 2017, now Pat. No. 10,631,782, which is a continuation of application No. 12/770,923, filed on Apr. 30, 2010, now Pat. No. 9,743,884.

(51) Int. Cl.
*A61B 5/00* (2006.01)

(52) U.S. Cl.
CPC .......... *A61B 5/4893* (2013.01); *A61B 5/4029* (2013.01)

(58) Field of Classification Search
CPC ..... A61B 5/4893; A61B 5/4029; A61B 34/10; A61B 5/7278; A61B 2018/00434; A61B 5/377; A61B 5/383; A61B 5/386; A61B 5/4035; A61B 5/4041; A61B 5/4047; A61B 5/4052; A61B 5/4824; A61B 5/4836

See application file for complete search history.

(56) References Cited

U.S. PATENT DOCUMENTS

| | | |
|---|---|---|
| 4,962,766 A | 10/1990 | Herzon |
| 5,178,145 A | 1/1993 | Rea |
| 5,284,154 A | 2/1994 | Raymond et al. |
| 5,775,331 A | 7/1998 | Raymond et al. |
| 6,132,386 A | 10/2000 | Gozani et al. |
| 6,132,387 A | 10/2000 | Gozani et al. |
| 6,259,945 B1 | 7/2001 | Epstein et al. |
| 6,266,558 B1 | 7/2001 | Gozani et al. |

(Continued)

OTHER PUBLICATIONS

Science Daily, "Nerve Mapping Technology Improves Surgery for Compressed Nerves," Science Daily, Mar. 23, 2013, 2 pages, https://www.sciencedaily.com/releases/2013/03/130323152444.htm.

(Continued)

*Primary Examiner* — David J. McCrosky
(74) *Attorney, Agent, or Firm* — Trop, Pruner & Hu, P.C.

(57) ABSTRACT

One embodiment includes a method for monitoring nerve tissue which includes inserting a dilator into muscle, the dilator including first and second electrodes at the distal tip. While the dilator is in muscle, a system may communicate (a) a first series of unequal current amplitude applications (e.g., a series including 0.5, 7, 3, 5 mA applications) to the first electrode to produce at least a first evoked potential (e.g., a MAP or NAP), and (b) a second series of unequal current amplitude applications to the second electrode to produce at least a second evoked potential. The method further includes sensing the first and second evoked potentials and determining a relative location of a nerve based on the sensing of at least one of the first and second evoked potentials.

17 Claims, 6 Drawing Sheets

(56) References Cited

U.S. PATENT DOCUMENTS

| | | | |
|---|---|---|---|
| 6,325,764 B1 * | 12/2001 | Griffith | A61B 5/4893 600/554 |
| 6,466,817 B1 | 10/2002 | Kaula et al. | |
| 6,493,588 B1 | 12/2002 | Malaney et al. | |
| 6,500,128 B2 | 12/2002 | Marino | |
| 6,609,018 B2 | 8/2003 | Cory et al. | |
| 6,810,281 B2 | 10/2004 | Brock et al. | |
| 7,104,965 B1 | 9/2006 | Jiang et al. | |
| 7,789,833 B2 | 9/2010 | Urbano et al. | |
| 9,022,948 B2 | 5/2015 | Wang | |
| 9,042,978 B2 | 5/2015 | Wu et al. | |
| 9,327,123 B2 | 5/2016 | Yamasaki et al. | |
| 9,622,684 B2 | 4/2017 | Wybo | |
| 9,743,884 B2 | 8/2017 | Rasmussen | |
| 10,016,142 B2 | 7/2018 | Block et al. | |
| 10,045,704 B2 | 8/2018 | Fagin et al. | |
| 2003/0105503 A1 | 6/2003 | Marino | |
| 2004/0199084 A1 | 10/2004 | Kelleher et al. | |
| 2005/0182454 A1 | 8/2005 | Gharib et al. | |
| 2006/0015162 A1 | 1/2006 | Edward et al. | |
| 2007/0016097 A1 | 1/2007 | Farquhar et al. | |
| 2008/0269634 A1 | 10/2008 | Young | |
| 2008/0281313 A1 | 11/2008 | Fagin et al. | |
| 2009/0105708 A1 | 4/2009 | Mcginnis et al. | |
| 2010/0010367 A1 | 1/2010 | Foley et al. | |
| 2012/0109004 A1 | 5/2012 | Cadwell | |
| 2013/0274614 A1 | 10/2013 | Shimada et al. | |
| 2014/0316268 A1 | 10/2014 | Kafiluddi et al. | |
| 2018/0028804 A1 | 2/2018 | Pianca | |
| 2018/0242910 A1 | 8/2018 | Marcotte et al. | |
| 2018/0289277 A1 | 10/2018 | Whittaker et al. | |
| 2018/0344244 A1 | 12/2018 | Botzer et al. | |

OTHER PUBLICATIONS

The Neurosurgery Spine Center, "Nerve Mapping," Dec. 5, 2017, 3 pages, https://www.neurosurgeryspinecenter.com/nerve-mapping/.

Raymond P. Onders, et al., "Mapping the phrenic nerve motor point: The key to a successful laparoscopic diaphragm pacing system in the first human series," Department of Surgery, University Hospitals of Cleveland, Cleveland, Ohio, Oct. 2004, 8 pages.

U.S. Patent and Trademark Office, Office Action dated Nov. 16, 2009 with Reply filed Feb. 16, 2010 in U.S. Appl. No. 11/745,505.

U.S. Patent and Trademark Office, Final Office Action dated Jul. 8, 2010 with Reply to Final filed Sep. 7, 2010, and Advisory Action dated Sep. 23, 2010 in U.S. Appl. No. 11/745,505.

Nuvasive, Creative Spine Technology, Maximum Access Surgical Platform, "XLIF Surgical Technique," Maxcess II, 2006, 26 pages.

Takatoma Moro, M.D., et al., "An Anatomic Study of the Lumbar Plexus With Respect to Retroperitoneal Endoscopic Surgery," SPINE vol. 28, No. 5, pp. 423-428, 2003.

Nuvasive, Creative Spine Technology, "XLIF eXtreme Lateral Interbody Fusion," 2006, nine pages, San Diego, Calif.

Cadwell, "Electrode & Accessories, Advancing Medical Technology To Help You, Help Others," p. 16.

A.F. Mellgren, et al., "Electromyography and Pudendal Nerve Terminal Motor Latency," 2nd ed. London: Springer-Vertag; 2006. pp. 105-109.

Cadwell Laboratories Inc., "Electrotrodes & Accessories," 2010, 60 pages.

* cited by examiner

DEVICES AND METHODS FOR NERVE MAPPING

This application is a continuation of U.S. patent application Ser. No. 15/685,960, filed Aug. 24, 2017, which is a continuation of U.S. patent application Ser. No. 12/770,923, filed Apr. 30, 2010, now U.S. Pat. No. 9,743,884, issued Aug. 29, 2017. The content of each of the above applications is hereby incorporated by reference

BACKGROUND

As described in "An Anatomic Study of the Lumbar Plexus with Respect to Retroperitoneal Endoscopic Surgery", SPINE Vol. 28, Number 5, pp. 423-428, 2003, by Takatomo Moro et al., nerve mapping can be critical during surgery, such as endoscopic surgeries, to treat various lumbar spine diseases. For example, retroperitoneal endoscopic surgery has been applied to anterior interbody fusion for disc herniation, anterior decompression and interbody fusion for burst fracture and discectomy for extreme lateral disc herniation. However, to perform such a surgery the psoas major muscle may be separated. Doing so generates a risk of injury to the lumbar plexus or nerve roots. Accurate nerve mapping is thus critical to avoid trauma to nerves, such as those exposed during dissection of the psoas muscle.

Various methods exist for monitoring nerves (i.e., nerve mapping) during surgical procedures. Such methods may determine when an electrified instrument is approaching a nerve. Specifically, a known current is communicated to the instrument. As the instrument is manipulated within or on the patient, the current may evoke a muscular response. The muscular response is recorded and an auditory and/or visual signal is produced which alerts the user, such as a physician, that the instrument is considered to be near the nerve coupled to the responsive muscle.

However, such methods do not provide the user with the location of the nerve evoking the muscular response. Instead, they only suggest a nerve is in the vicinity of the instrument. Also, to record the muscular response the responsive muscle must not be numbed or temporarily paralyzed with, for example, neuromuscular blockade agents. As a result, the user may have difficulty advancing the instrument through a muscle that is not only active (i.e., not paralyzed), but which may even be contracting to resist or fight the user's efforts.

BRIEF DESCRIPTION OF THE DRAWINGS

Features and advantages of the present invention will become apparent from the appended claims, the following detailed description of one or more example embodiments, and the corresponding figures, in which:

DETAILED DESCRIPTION

Figure 1A:
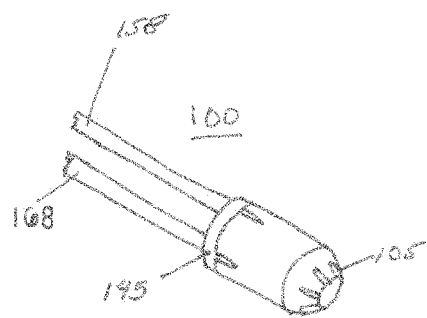
FIGS. 1A-1D include a dilator in one embodiment of the invention.
Figure 1B:
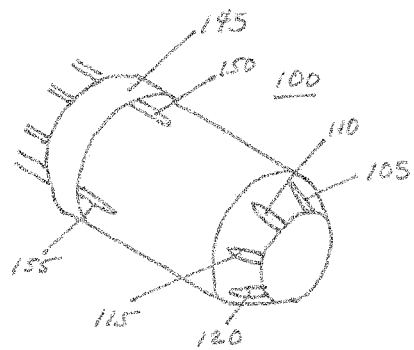
Figure 1C:
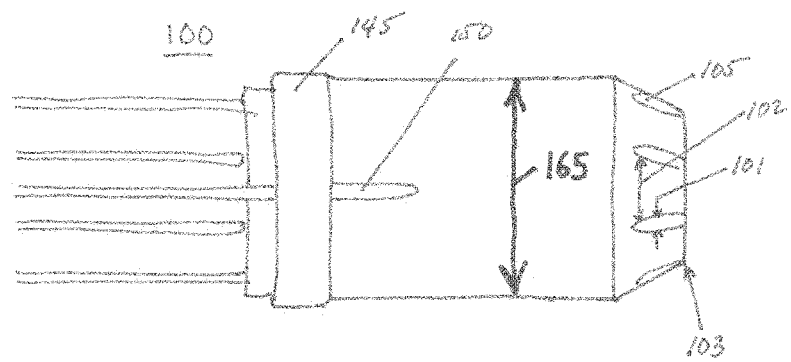
Figure 1D:
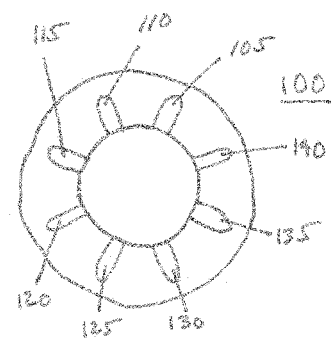

In the following description, numerous specific details are set forth. However, it is understood that embodiments of the invention may be practiced without these specific details. Well-known circuits, structures, and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features (utilized in the same or differing orientations and orders) described for other embodiments. Also, as used herein "first", "second", "third" and the like describe a common object and indicate that different instances of like objects are being referred to. Such adjectives are not intended to imply the objects so described must be in a given sequence, either temporally, spatially, in ranking, or in any other manner. The terms "coupled" and "connected," along with their derivatives, are not intended as synonyms for each other. Rather, in particular embodiments, "connected" may be used to indicate that two or more elements are in direct physical or electrical contact with each other. "Coupled" may mean that two or more elements co-operate or interact with each other, but they may or may not be in direct physical or electrical contact.

FIGS. 1A-D include various renderings of dilator 100 in an embodiment of the invention. Dilator 100 may include electrodes 105, 110, 115, 120, 125, 130, 135, and 140 that connect to a distal tip 103 of the device. As used herein "tip" constitutes a leading edge of device 100. The electrodes may indeed wrap around tip 103. As will be described more fully below, locating the electrodes most distally may ensure any initial forward advancing contact or approach to a nerve is identified at the earliest instance (as compared to a case where an electrode is located proximal to leading edge 103). Embodiments of the invention are not limited to having eight electrodes and may instead include one (e.g., unipolar), two, three, four, five, six, seven, nine, ten (and so on) electrodes. Each electrode may be dimensioned alike. Taking electrode 105 for example, electrode 105 may have a 3 mm width 101. Other embodiments may include electrode with widths of 1, 2, 4, 5 mm (and so on). The electrodes may be spaced a distance 102, such as 8 mm for example, from one another. The electrodes may have various shapes including circular, rectangular, square, oblong, and the like.

Ground electrode 145 is located on dilator 100. Ground 145 may be located, for example, 30 mm proximal of the proximal edge or tip of electrode 105. In other embodiments ground electrode 145 may be located 40 mm proximal from electrode 105 and still other embodiments may distance the electrodes at 100 mm, 200 mm, 300 mm, and so on. Electrode 145 may be formed as a 6 mm wide band that traces a perimeter of dilator 100. Of course ground electrode 145 need not trace the entire perimeter of device 100 in other embodiments. For example, ground electrode 145 may be located in one or more sections on device 100, none of which constitute a continuous ring that traces the entire perimeter of dilator 100. Outer diameter 165 of dilator 100 may be 25 mm but other embodiments are not so limited.

Figure 1E:
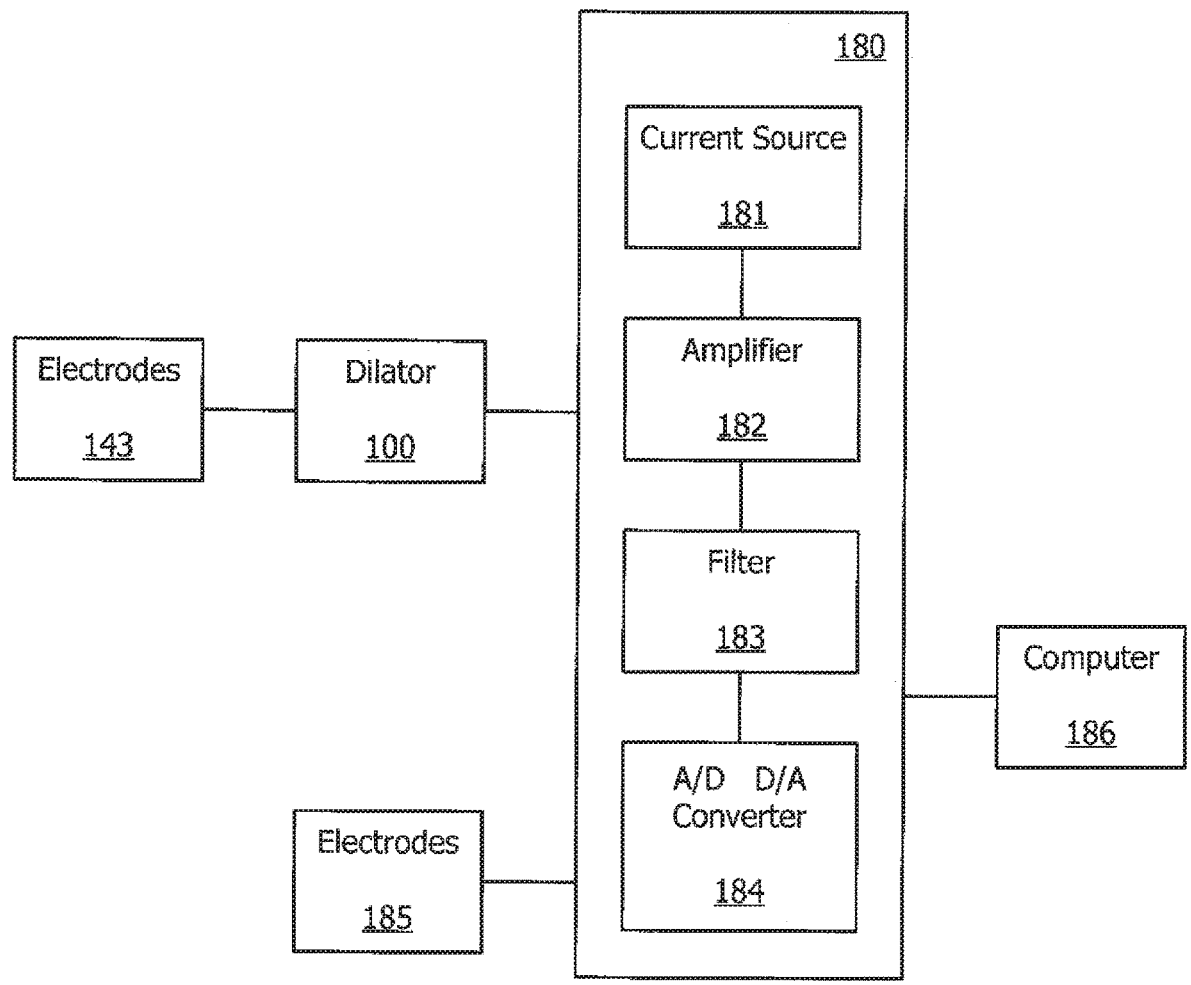
FIG. 1E includes a stimulation and/or sensing system in an embodiment of the invention.

Device 100 may include recesses 150, 155 to allow components to snap fit onto device 100 with a "one way fit only" contact clip to be attached to the dilator or a "coded" connector providing the interface between the hardware and stimulation and/or sensing system 195 (FIG. 1E). Dilator 100 may have various shapes or cross-sections including circular, rectangular, square, oblong, and the like. Also, device 100 may include members 158, 168 that mate with differently sized dilators, guide wires, shims, and the like. Device 100 could be a disposable single use attachment to other dilators or devices.

Figure 6:
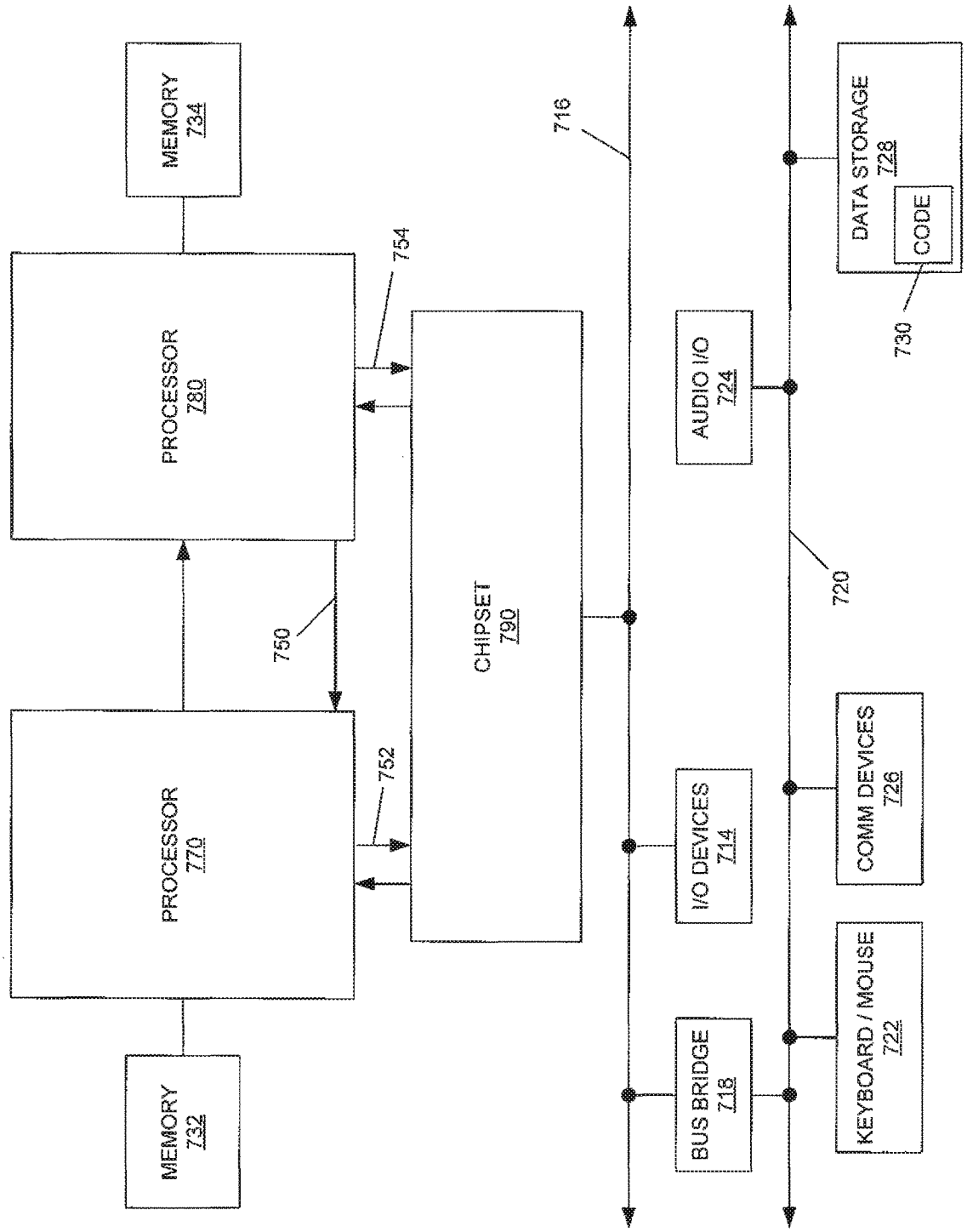
FIG. 6 includes a system for operation with an embodiment of the invention.

FIG. 1E includes stimulation and/or sensing system 195 in an embodiment of the invention. Electrodes 143 may include electrodes 105, 110, 115, 120, 125, 130, 135, 140, and 145 located on dilator 100. Dilator 100 and electrodes 185 (e.g., surface patch and/or sub-dermal needle) both communicate with unit 180. Unit 180 includes a current source 181 for communicating current to any of electrodes 143, 185; amplifier unit 182 for amplifying signals from electrodes 143, 185; filter(s) 183 and general signal processing circuitry, such as analog/digital and digital/analog converter 184, for processing signals from electrodes 143, 185. Unit 180 communicates with computer system 186 (FIG. 6). The use of system 195 is discussed further below.

Figure 2:
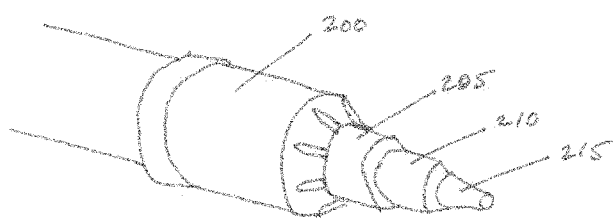
FIG. 2 includes a nested dilator system in an embodiment of the invention.

FIG. 2 includes dilator 200 in an embodiment of the invention. Dilator 200 is shown nested over progressively smaller dilators 205, 210, and 215. Various embodiments may include dilators that nest over more or fewer dilators. Also, dilator 200 may nest within, over, or couple to other dilators or devices, such as probes, retractors, snips, cutting devices, rasps, trocars, spreaders, distracters, shims, scrapers, chisels, disc cutters, curettes, suction probes, tamps, and the like. A system may include one, two, three, four, five (and so on) nested dilators. All of the dilators, or just some of the dilators, may include electrodes as described above (e.g., electrodes 105, 110, 115, 120, 125, 130, 135, 140, 145).

Embodiments described herein, such as device 100, may be used in various surgical approaches. For example, dilator 100 may be used in various retroperitoneal space procedures such as a lateral interbody fusion (LIF) procedure where the spine is approached from the side of the patient. Lumbar interbody fusion may entail fusing vertebrae together to reduce their motion after possibly removing some or the entire intervertebral disc located between the fused vertebrae. An intervertebral spacer may replace the removed disc material. Approaching laterally and via endoscopic means allows for potentially less trauma to muscles, ligaments, blood vessels, and/or organs as opposed to techniques such as posterior, transforaminal, or anterior interbody fusion. Approaching laterally still provides good access to the spinal column such as may be needed for fusion at lumbar levels L1 through L5. There are many indications for LIF such as, for example, degenerative disc disease, recurrent disc herniation, post-laminectomy syndrome, adjacent level syndrome, degenerative spondylolisthesis, degenerative scoliosis, and posterior pseudarthrosis. Thus, retroperitoneal endoscopic surgery (e.g., LIF) may be applied to various spinal disorders.

However, such procedures may require the user to traverse muscles, such as the psoas major muscle, in order to access the spine. When the psoas muscle is separated during retroperitoneal endoscopic surgery, there is a potential risk of injury to the lumbar plexus or nerve roots. Thus, in an embodiment dilator 100 is inserted into psoas muscle to facilitate nerve mapping.

Figure 3:
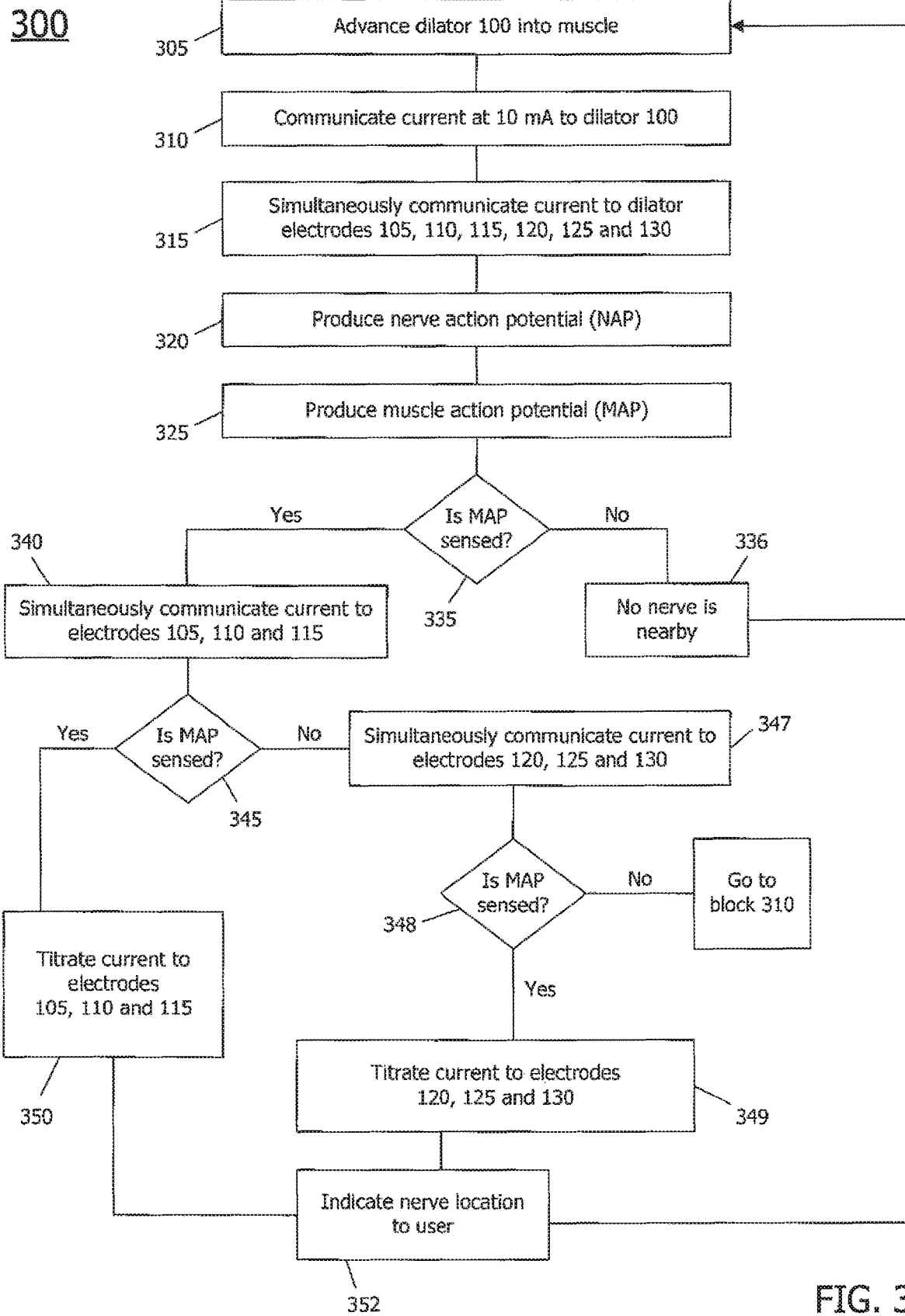
FIGS. 3-5 include methods for nerve mapping in embodiments of the invention.

FIG. 3 includes a method 300 in an embodiment of the invention. In block 305 a user inserts dilator 100 into muscle, such as the psoas muscle. As the user advances dilator 100 through the psoas muscle and towards the spinal column, care must be taken to detect neighboring nerves. Thus, in block 310 current is communicated to dilator 100. Specifically, current may be supplied to any or all of electrodes 105, 110, 115, 120, 125, 130, 135, and 140. Doing so may result in a muscle action potential (MAP) from the level of related muscle groups.

For example, in block 315 current is simultaneously supplied to distal tip electrodes 105, 110, 115, 120, 125, 130. These electrodes may be designated as cathodes. Other electrodes, such as electrodes 135, 140, may be designated as anodes. Current may be delivered to patient tissue via electrodes 105, 110, 115, 120, 125, 130. For example, 10 mA from a Constant Current Stimulation (CCS) device may be supplied with a stimulus rate of 9.7 cycles/second (Hz) at a duration of 200 microseconds. Should one of the cathodes be functionally proximate to a nerve the stimulation current may depolarize the nerve and produce a nerve action potential (NAP) volley (block 320). The NAP may in turn produce a MAP (block 325) in the muscle(s) related to the affected nerve. In other embodiments other electrodes (e.g., electrode 105), no electrodes, electrodes located elsewhere on device 100 (proximal to end 103 and located along shaft of device 100), or electrodes located elsewhere on the body (e.g., needle or surface electrode) may serve as anodes or references.

In an embodiment, in diamond 335 a determination is made regarding whether a MAP is being sensed or recorded. The MAP may be recorded using, for example, Disposable Sub-dermal Needles (DSNs) inserted into tissue (e.g., muscle, fat, facie, and the like) and/or surface patch electrodes. For example, two DSNs may be inserted into or near one or more of the following muscles including, without limitation, the vastus lateralis, gastrocnemius, anterior tibialis, abductor hallucis longus muscles and the like. The MAP may be sensed from each or some of the monitored muscles. In order to create a MAP that can be measured, the monitored muscles should not be subject to muscle relaxants at a level that would inhibit detection of MAPs. Amplifier filters 183 may be set to allow signals at 30 Hz-2,000 Hz for each recording channel with 50 microvolts/division for resolution.

If no MAP is sensed, in block 336 a determination is made that no nerve is nearby and device 100 may be moved within the muscle. For example, the device may be moved from a stationary position or continued along a path already being traversed. If a MAP is sensed, electrodes 120, 125, and 130 may be electronically disconnected from current using, for example, a multiplexor. In block 340 current is then supplied simultaneously to only electrodes 105, 110, and 115 while electrodes 135, 140 may be designated as anodes. Current may again be supplied at, for example, 10 mA. In diamond 345, a determination is made regarding whether a MAP is sensed. For example, a determination may be made regarding whether a MAP exceeding a threshold of 50 microvolts is detected. If a MAP is sensed, in block 350 current may be supplied to electrodes 105, 110, 115 in various ways of titration.

As one example of current titration, in block 350 0.5 mA is provided to electrode 105, then to electrode 110, and then to electrode 115. In other words, the current is supplied non-simultaneously to these electrodes. If no resultant MAP is detected resulting from any of the 0.5 mA current applications, a higher current level (e.g., 7 mA) may be supplied sequentially (i.e., non-simultaneously) to each of electrodes 105, 110, 115. If no MAP is detected based on the administration of 7 mA, a current level higher than the immediately preceding 7 mA level (e.g., 8.5 mA) may be supplied sequentially to each of electrodes 105, 110, 115. If a MAP is detected for only one of electrodes 105, 110, 115 based on the administration of 7 mA, then the electrode that led to the MAP is determined to be closest to a nerve. However, if two or more electrodes, such as three electrodes 105, 110, 115, each produce a MAP based on the administration of 7 mA, then a current level lower than the immediately preceding current level (i.e., 7 mA) may be supplied sequentially to each of target electrodes 105, 110, 115. For example, 5 mA may be sequentially supplied to the three electrodes. The titrating process then continues for those three electrodes. If no resultant MAP is detected resulting from 5 mA current applications, a higher current level (e.g., 6 mA) may be supplied sequentially to each of electrodes 105, 110, 115. If a MAP is detected for only one of electrodes 105, 110, 115 based on the administration of 5 mA, then the electrode that led to the MAP is determined to be closest to a nerve. However, if two or more electrodes, such as all three electrodes, produce a MAP based on the administration of 5 mA, then a current level lower than the immediately preceding current level (i.e., 5 mA) may be supplied sequentially to each of target electrodes 105, 110, 115. For example, 3 mA may be sequentially supplied to the three electrodes. The titrating process then continues. On the other hand, if instead of three electrodes producing a MAP based on the administration of 5 mA, only two electrodes produce a MAP based on the administration of 5 mA, then a current level lower than the immediately preceding current level (i.e., 5 mA) may be supplied sequentially to only those two electrodes. For example, 3 mA may be sequentially supplied to only the two electrodes at issue. The titrating process then continues.

As another example of current titration, in block 350 a sequential series of stimulation may be provided to electrode 105 starting at 0.5 mA and increased in 0.25 mA steps until a MAP is detected and/or an upper threshold (e.g., 10 mA) is reached. When a MAP is first sensed, the corresponding current level is noted. This sequence is repeated for electrodes 110 and 115. The contact point among electrodes 105, 110, 115 closest to the nerve may be deemed to be the electrode or point that needs the least amount of current to produce a recorded or sensed MAP.

In diamond 345, if no MAP is sensed then in block 347 electrodes 105, 110, and 115 are disconnected from current and current is communicated to electrodes 120, 125, and 130. In diamond 348, a determination is made to see if a MAP is detected. If not, the method proceeds to block 310 for retesting. If a MAP is sensed based on current supplied to electrodes 120, 125, and 130, then current may be supplied in a titrated form to those electrodes in a manner similar to block 350. For example, in block 349 0.5 mA is provided to electrode 120, then to electrode 125, and then to electrode 130. If no resultant MAP is detected resulting from any of the 0.5 mA current applications, a higher current level (e.g., 7 mA) may be supplied sequentially (i.e., non-simultaneously) to each of electrodes 120, 125, and 130. If no MAP is detected based on the administration of 7 mA, a current level higher than the immediately preceding 7 mA level (e.g., 8.5 mA) may be supplied sequentially to each of electrodes 120, 125, and 130. If a MAP is detected for only one of electrodes 120, 125, and 130 based on the administration of 7 mA, then the electrode that led to the MAP is determined to be closest to a nerve. However, if two or more electrodes, such as all three electrodes, produce a MAP based on the administration of 7 mA, then a current level lower than the immediately preceding current level (i.e., 7 mA) may be supplied sequentially to each of the target electrodes 120, 125, and 130. For example, 5 mA may be sequentially supplied to the three electrodes. The titrating process then continues. If no resultant MAP is detected resulting from 5 mA current applications, a higher current level (e.g., 6 mA) may be supplied sequentially to each of electrodes 120, 125, and 130. If a MAP is detected for only one of electrodes 120, 125, and 130 based on the administration of 5 mA, then the electrode that led to the MAP is determined to be closest to a nerve. However, if two or more electrodes, such as three electrodes, produce a MAP based on the administration of 5 mA, then a current level lower than the immediately preceding current level (i.e., 5 mA) may be supplied sequentially to each of the target electrodes 120, 125, and 130. For example, 3 mA may be sequentially supplied to the three electrodes. The titrating process then continues.

As another example of current titration, in block 349 a sequential series of stimulation is provided to electrode 120 starting at 0.5 mA and increased in 0.25 mA steps until a MAP is detected and/or an upper threshold (e.g., 10 mA) is reached. When a MAP is first sensed, the current level is noted. This sequence is repeated for electrodes 125 and 130. The contact point among electrodes 120, 125, and 130 closest to the nerve will be the electrode or point that needs the least amount of current to produce a recorded or sensed MAP.

Blocks 349 and 350 lead to block 352. In block 352, the nerve location is indicated to the user. For example, the indication may include a graphical user interface (GUI) that indicates the relative nerve location in relation to device 100 and/or to particular electrodes on device 100 (e.g., proximal, distal, anterior, posterior, inferior, superior, and the like). The user may then "steer device 100 away" from the electrode highlighted by the GUI as being problematically close to a nerve. Auditory alarms (e.g., beep) and visual alarms (e.g., flashing red indicator) may be used to indicate grades of proximity to nerves (e.g., continuous beep and/or rapid blinking red indicator upon close range of device 100 to a nerve). Such a feedback mechanism may be applicable to any of the many embodiments disclosed herein.

In some embodiments titrated current may be supplied to all electrodes such as, for example, electrodes 105, 110, 115, 120, 125, 130. In an embodiment method 300 is altered to move directly from block 335 "yes" path to non-simultaneously providing titrated current to each of electrodes 105, 110, 115, 120, 125, 130. In this embodiment as well as others, titrated current may even be supplied to electrodes 135, 140 by designating other electrodes as anodes or references, even if only for a temporary period. As indicated in block 352, nerve location may still be determined based on which electrode had the lowest threshold for producing a MAP. Also, embodiments do not necessarily require determining which single electrode has the lowest threshold for producing a MAP or NAP. For example, merely determining that any of two or three electrodes (e.g., 105 and 110) has a lower threshold than other electrodes (e.g., 125, 130) may provide enough precision to still guide a user away from problematic areas. An embodiment may allow the user to configure the level of specificity he or she wants. Of course, the titration sequencing may occur so quickly that there is little appreciable burden associated with high specificity determination, thereby lowering the need to configure the system for lower specificity. This applies to other embodiments described herein, such as the embodiment of FIG. 5 discussed below.

Repeating the current titration while device 100 is not moved may serve to confirm the findings. System 195 may automatically repeat the sequence continually or the sequence of method 300, or modifications thereof, may be repeated upon user command. Also, rotating or moving device 100 may also confirm the findings as the nerve should accordingly be closest to another electrode depending on the movement of device 100 (e.g. rotation of device 100). The method then returns to block 305 as the user adjusts the dilator away from any impending nerves and moves dilator 100 to a spot on the spinal column, such as the annulus, where the fusion procedure may continue (e.g., nucleus and annulus partial or complete removal, spacer implant, and the like). Other devices (e.g., tissue retractors) may be advanced over or through the dilator to provide instrument access to the disc space.

Figure 4:
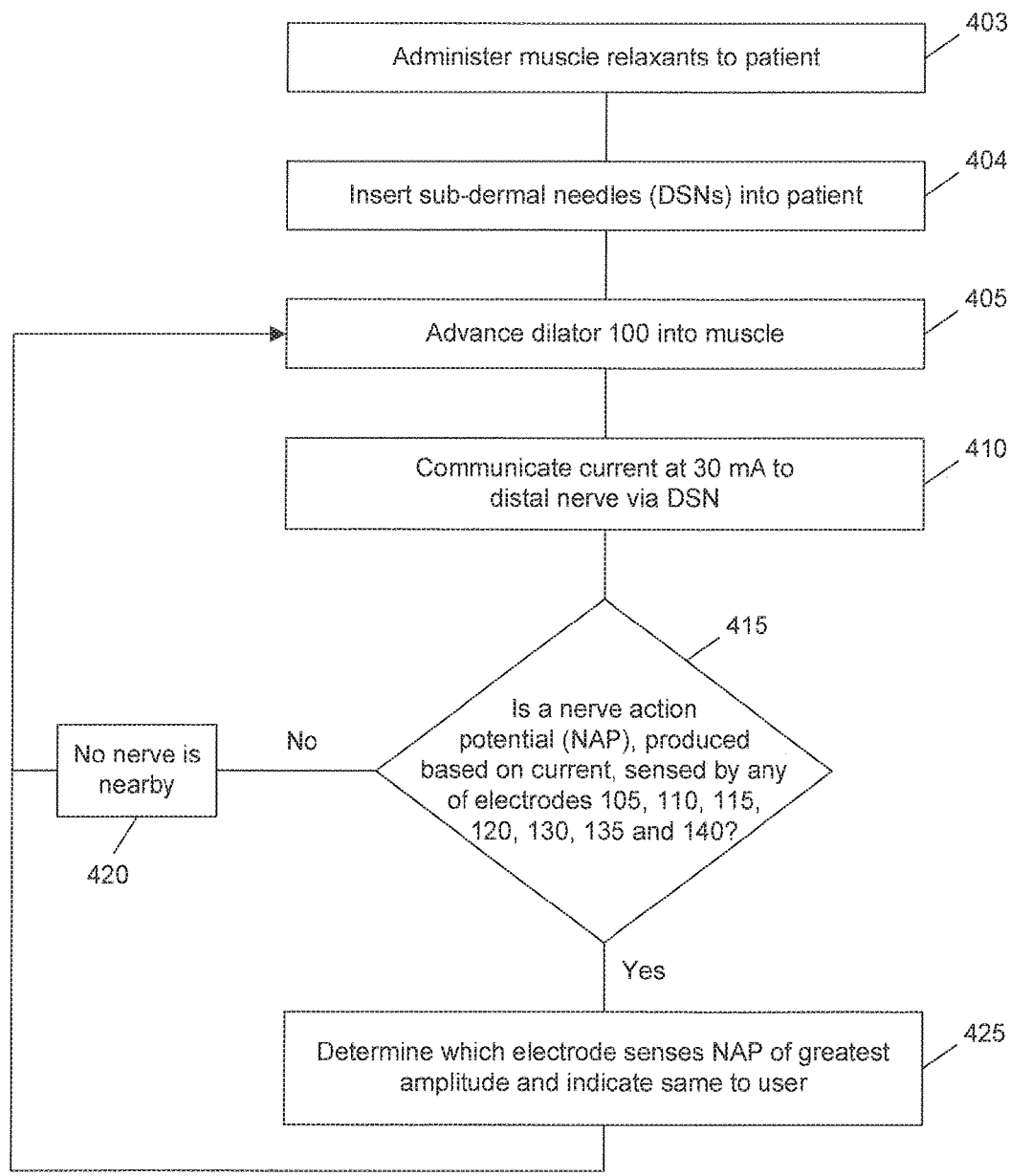

FIG. 4 includes a method 400 in an embodiment of the invention. In block 403 muscle relaxants may be administered to the patient. The relaxant, such as succinolcholine, vecuronium, and/or rocuronium, may be supplied at a level such that the relaxant relaxes one or more of the following muscles including the iliocostalis thoracis, iliocostalis lumborum, spinalis thoracis, internal/external obliques, psoas, multifidus, and intertransversarii lumborum muscles and the like. As a result, the user does not need to fight against various muscles partially contracting, or contracting at full force, during the procedure. In block 404 two sub-dermal needle electrodes (e.g., DSNs) are used. Two DSNs (e.g., cathode and anode) are inserted close or functionally proximate to a nerve, such as one or more of the following nerves: iliohypogastric, ilioinguinal, lateral femoral cutaneous, genitofemoral, femoral, obturator, sciatic, tibial, peroneal, lumbosacral plexus nerves and the like.

In block 405 a user inserts dilator 100 into muscle, such as, for example, the psoas muscle during a LIF procedure. As dilator 100 advances through the psoas muscle care must be taken to detect neighboring nerves. Thus, in block 410 current, at a known energy level such as 20, 25, 30, 35, 40, or 45 mA, is communicated to a distal nerve (e.g., sciatic or femoral nerves) via the DSN(s). The stimulus rate may be 11.1 cycles/second (Hz) for a duration of 300 microseconds. Communicating the energy to the distal nerve(s) may result in a NAP(s) that is detected in one or more electrodes 105, 110, 115, 120, 125, 130, 135, and 140. Sensing a NAP, instead of a MAP, may be required if the muscle relaxant given the patient is such that evoked potentials cannot be monitored by sensing MAPs from the paralyzed muscles. Each electrode of device 100 may communicate with a separate channel on a monitoring device. Electrodes 135 and 140 may be designated as reference electrodes, although in other embodiments electrode 105 is the sole reference and in still other embodiments electrodes 105, 110, 115, 120 (and so on) constitute multiple references. The remaining electrodes 105, 110, 115, 120, 125, and 130 may be free to sense NAPs.

In diamond 415, a determination is made regarding whether any of electrodes 105, 110, 115, 120, 125, 130, 135, and 140 has detected a NAP resulting from the stimulus current. If no, in block 420 a determination is made that no nerve is nearby and the user may further advance device 100 from a static location or continue along trajectory already being traversed. However, in block 425 if a NAP is detected the electrode closest to the nerve will be the point that senses a NAP of the highest amplitude.

An indication may be given to the user as to which electrode recorded the highest amplitude. The indication may include the aforementioned GUI that indicates the nerve location in relation to an electrode of device 100. Auditory and visual alarms may be used to indicate grades of proximity to nerves.

By repeating, automatically or manually, the current application described in block 410, while device 100 is not moved, may serve to confirm the findings. Also, rotating or moving device 100 may also confirm the findings as the nerve should accordingly be closest to another electrode depending on the movement of device 100. The user may then adjust dilator 100 away from any impending nerves and to a spot on the spinal column where the fusion procedure may continue. Other devices may be advanced via (e.g., over or within) the dilator to provide instrument access to the disc space.

Figure 5:
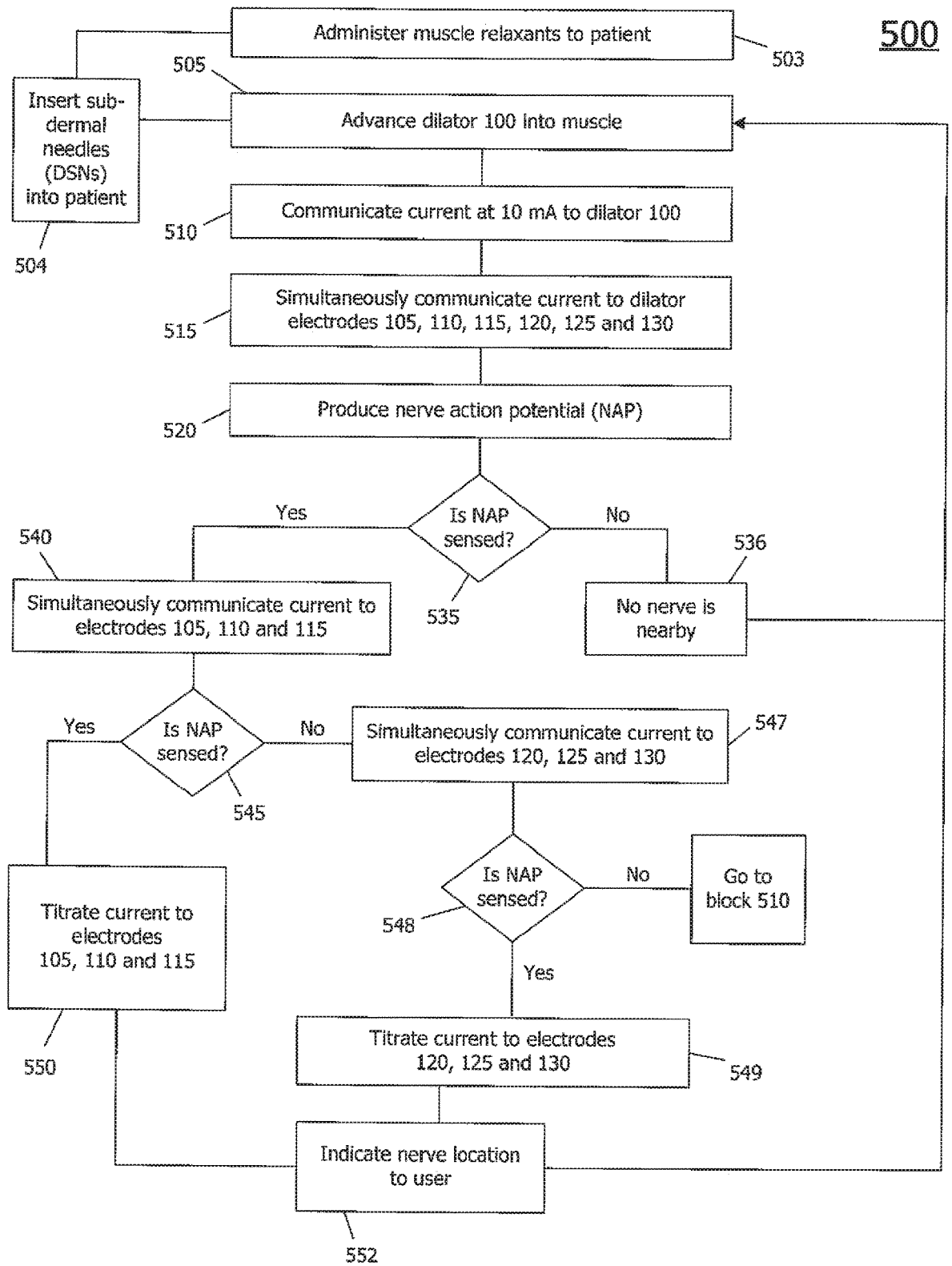

FIG. 5 includes a method 500 in an embodiment of the invention. In block 503 muscle relaxants may be administered to the patient to relax various muscles, such as those described above. In block 504 two DSNs are inserted close to a nerve, such as those discussed above. In block 505 a user inserts dilator 100 into muscle, such as the psoas muscle. As the user advances dilator 100 through the psoas muscle and towards the spinal column, care must be taken to detect neighboring nerves. Thus, in block 510 current, such as 10 mA, is communicated to dilator 100. Specifically, current may be supplied to any or all of electrodes 105, 110, 115, 120, 125, 130, 135, and 140.

For example, in block 515 current is simultaneously supplied to distal tip electrodes 105, 110, 115, 120, 125, 130. These electrodes may be designated as cathodes. Other electrodes, such as electrodes 135, 140 may be designated as anodes. Current may be delivered to patient tissue via electrodes 105, 110, 115, 120, 125, 130 using known energy levels, such as 10, 20, 25, 30, 35, 40, or 45 mA, produced from a CCS device. In this example, 10 mA is used with a stimulus rate of 11.1 cycles/second (Hz) for a duration of 200 microseconds. Should one of the cathodes be functionally proximate to a nerve the stimulation current may depolarize the nerve and produce a NAP volley (block 520).

In diamond 535 a determination is made regarding whether a NAP is being sensed or recorded. The NAP may be recorded using two DSNs located close to nerves (e.g., located in fat, facie, muscle, and various other tissues) such as those tissues listed above. Amplifier filters 183 may be set to allow signals at 30 Hz-2,000 Hz for each recording channel with 50 microvolts/division for resolution.

If no NAP is sensed, in block 536 a determination is made that no nerve is nearby and device 100 may be moved within the muscle. However, if a NAP is sensed, electrodes 120, 125, and 130 may be disconnected from current. In block 540 current is then supplied simultaneously to only electrodes 105, 110, and 115 while electrodes 135, 140 may be designated as anodes. Current may again be supplied at 10 mA. In diamond 545, a determination is made regarding whether a NAP is sensed. If a NAP is sensed, in block 550 current may be supplied in a titrated form.

As one example of current titration, in block 550 0.5 mA is provided to electrode 105, then to electrode 110, and then to electrode 115. In other words, the current is supplied non-simultaneously to these electrodes. If no resultant NAP is detected resulting from any of the 0.5 mA current applications, a higher current level (e.g., 7 mA) may be supplied sequentially (i.e., non-simultaneously) to each of electrodes 105, 110, 115. If no NAP is detected based on the administration of 7 mA, a current level higher than the immediately preceding 7 mA level (e.g., 8.5 mA) may be supplied sequentially to each of electrodes 105, 110, 115. If a NAP is detected for only one of electrodes 105, 110, 115 based on the administration of 7 mA, then the electrode that led to the NAP is determined to be closest to a nerve. However, if two or more electrodes, such as three electrodes, produce a NAP based on the administration of 7 mA, then a current level lower than the immediately preceding current level (i.e., 7 mA) may be supplied sequentially to each of the target electrodes 105, 110, 115. For example, 5 mA may be sequentially supplied to the three electrodes. The titrating process then continues. Other current titration methods are possible. For example, a sequential series of stimulation is provided to electrode 105 starting at 0.5 mA and increased in 0.25 mA steps until a NAP is detected and/or an upper threshold is reached. When a NAP is first sensed, the current level is noted. This sequence is repeated for electrodes 110 and 115. The contact point among electrodes 105, 110, 115 closest to the nerve will be the electrode or point that needs the least amount of current to produce a recorded or sensed NAP.

In diamond 545, if no NAP is sensed then in block 547 electrodes 105, 110, and 115 are disconnected from current and current is communicated to electrodes 120, 125, and 130. In diamond 548, a determination is made to see if a NAP is detected. If not, the method proceeds to block 510 for retesting. If a NAP is sensed based on current supplied to electrodes 120, 125, and 130, then current may be supplied in a titrated form to those electrodes in a manner similar to block 550. For example, in block 549 0.5 mA is provided to electrode 120, then to electrode 125, and then to electrode 130. If no resultant NAP is detected resulting from any of the 0.5 mA current applications, a higher current level (e.g., 7 mA) may be supplied sequentially (i.e., non-simultaneously) to each of electrodes 120, 125, and 130. If no NAP is detected based on the administration of 7 mA, a current level higher than the immediately preceding 7 mA level (e.g., 8.5 mA) may be supplied sequentially to each of electrodes 120, 125, and 130. If a NAP is detected for only one of electrodes 120, 125, and 130 based on the administration of 7 mA, then the electrode that led to the NAP is determined to be closest to a nerve. However, if two or more electrodes, such as three electrodes, produce a NAP based on the administration of 7 mA, then a current level lower than the immediately preceding current level (i.e., 7 mA) may be supplied sequentially to each of the target electrodes 120, 125, and 130. For example, 5 mA may be sequentially supplied to the three electrodes. The titrating process then continues. As another example of current titration, in block 549 a sequential series of stimulation is provided to electrode 120 starting at 0.5 mA and increased in 0.25 mA steps until a NAP is detected and/or an upper threshold is reached. When a NAP is first sensed, the current level is noted. This sequence is repeated for electrodes 125 and 130. The contact point among electrodes 120, 125, and 130 closest to the nerve will be the electrode or point that needs the least amount of current to produce a recorded or sensed NAP.

Blocks 549 and 550 lead to block 552. In block 552, the nerve location is indicated to the user using, for example, embodiments described above.

In some embodiments titrated current may be supplied to all electrodes such as, for example, electrodes 105, 110, 115, 120, 125, 130. In an embodiment method 500 is altered to move directly from block 535 "yes" path to non-simultaneously providing titrated current to each of electrodes 105, 110, 115, 120, 125, 130. In this embodiment as well as others, titrated current may even be supplied to electrodes 135, 140 by designating other electrodes as anodes or references, even if only for a temporary period. As indicated in block 552, nerve location may still be determined based on which electrode had the lowest threshold for producing a NAP.

Repeating the current titration while device 100 is not moved may serve to confirm the findings. System 195 may automatically repeat the sequence continually or the sequence of method 500, or modifications thereof, may be repeated upon user command. Also, rotating or moving device 100 may also confirm the findings as the nerve should accordingly be closest to another electrode depending on the movement of device 100. The method then returns to block 505 as the user adjusts the dilator away from any impending nerves and moves dilator 100 to a spot on the spinal column, such as the annulus, where the fusion procedure may continue (e.g., nucleus and annulus partial or complete removal, spacer implant, and the like). Other devices (e.g., tissue retractors) may be advanced over the dilator to provide instrument access to the disc space.

Thus, using embodiments described herein may facilitate locating a safety zone for, as an example, the lumbar plexus and nerve roots when performing LIF or other procedures. These safety zones may be located at, for example, L2-L3 and above, between the cranial third of the L3 vertebral body and L4-L5 (noting the genitofemoral nerve located anteriorly of the center of the vertebral body). Fusion or work regarding L1-L3 may be coupled with monitoring or stimulating the lateral femoral cutaneous nerve. Work regarding L4, L5, S1, or S2 may be coupled with monitoring or stimulating the sciatic nerve.

Thus, one embodiment includes a method for monitoring nerve tissue which includes inserting a dilator into muscle (e.g., psoas muscle during a LIF procedure), the dilator including a distal end portion including first and second electrodes. The electrodes may be at the distal tip, wrap around the tip, or be located entirely proximal of the tip but still located in the distal region of the dilator. While the dilator is in muscle, a system may communicate (a) a first series of unequal current amplitude applications (e.g., a series including 0.5, 7, 3, 5 mA applications) to the first electrode to produce at least a first evoked potential (e.g., MAP or NAP), and (b) a second series of unequal current amplitude applications to the second electrode to produce at least a second evoked potential. The method may further include sensing the first and second evoked potentials and determining a relative location of a nerve based on the sensing of at least one of the first and second evoked potentials. In an embodiment, the relative location is relative to one or more electrodes of the dilator. In an embodiment, if the first potential is produced using a lower current level than that which produced the second potential, the nerve may be determined to be closer to the first electrode. Embodiments that include communicating a series of unequal current amplitude applications to an electrode may include titrating current to the electrode to determine a current amplitude needed to produce the first evoked potential. Titrating may be done forwards, backwards, or combinations thereof. For example, titrating may progress up from a low current to a high current, from a high current to a low current, or between high and low currents to thereby box in a response of interest.

Embodiments described herein are not limited to dilators and may instead be implemented with devices and equipment such as, for example, probes, retractors, snips, cutting devices, rasps, trocars, spreaders, distracters, shims, scrapers, chisels, disc cutters, curettes, suction probes, tamps, and the like, which are inserted into innervated areas of the body that call for nerve mapping. For example, electrodes 105, 110, 115, 120, 125, 130, 135, and 140 could be located along the leading distal edge of such devices, such as a probe. The probe could be used to conduct nerve mapping, as explained herein, before, after, or independent of use of dilator 100. For example, the probe could be used, after dilator or dilators have been used, to further explore tissue that may still be in the surgical field despite use of the dilator(s).

Ground electrode 145 could be located proximal to electrodes 105, 110, 115, 120, 125, 130, 135, and 140 or off device 100 entirely. Also, embodiments are not limited to LIF but may be implemented treating various disorders with procedures (e.g., endoscopic procedures), related or unrelated to spinal therapy, that would benefit from nerve mapping.

Embodiments may be implemented in many different system types. Referring now to FIG. 6, shown is a block diagram of a system in accordance with an embodiment of the present invention. Multiprocessor system 700 is a point-to-point (P-P) interconnect system and includes first processor 770 and second processor 780 coupled via point-to-point interconnect 750. Each of processors 770 and 780 may be multicore processors. The term "processor" may refer to any device or portion of a device that processes electronic data from registers and/or memory to transform that electronic data into other electronic data that may be stored in registers and/or memory. First processor 770 may include a memory controller hub (MCH) and P-P interfaces. Similarly, second processor 780 may include a MCH and P-P interfaces. The MCHs may couple the processors to respective memories, namely memory 732 and memory 734, which may be portions of main memory (e.g., dynamic random access memory (DRAM)) locally attached to the respective processors. First processor 770 and second processor 780 may be coupled to chipset 790 via P-P interconnects 752, 754 respectively. Furthermore, chipset 790 may be coupled to first bus 716 via an interface. Various input/output (I/O) devices 714 may be coupled to first bus 716, along with bus bridge 718, which couples first bus 716 to second bus 720. Various devices may be coupled to second bus 720 including, for example, keyboard/mouse 722, communication devices 726, and data storage unit 728 (e.g., disk drive or other mass storage device that includes code 730). Further, audio I/O 724 may be coupled to second bus 720.

Embodiments may be implemented in code and may be stored on a storage medium having stored thereon instructions which can be used to program a system to perform the instructions. The storage medium may be non-transitory and may include, but is not limited to, any type of disk including floppy disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as DRAMs, static random access memories (SRAMs), erasable programmable read-only memories (EPROMs), flash memories, electrically erasable programmable read-only memories (EEPROMs), magnetic or optical cards, or any other type of media suitable for storing electronic instructions. Such computer-readable or computer-usable storage medium or media is (are) considered to be part of an article (or article of manufacture). An article or article of manufacture can refer to any manufactured single component or multiple components.

Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. The terms "code" or "program" cover a broad range of components and constructs, including applications, drivers, processes, routines, methods, modules, and subprograms. Thus, the terms "code" or "program" may be used to refer to any collection of instructions which, when executed by a processing system, performs a desired operation or operations. In addition, alternative embodiments may include processes (in code or otherwise) that use fewer than all of the disclosed operations, processes that use additional operations, processes that use the same operations in a different sequence, and processes in which the individual operations disclosed herein are combined, subdivided, or otherwise altered.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A system to monitor nerve tissue comprising:
   a surgical instrument including a distal end portion coupled to first, second, third, and fourth electrodes;
   a memory;
   a processor, coupled to the memory, configured to cause a current source unit to:
   (a) simultaneously communicate a first current application to the first electrode, a second current application to the second electrode, a third current application to the third electrode, and a fourth current application to the fourth electrode;
   (b) sense a first evoked response to any of the first, second, third, and fourth current applications when the first evoked response occurs;
   (c) when no evoked response to the first, second, third, and fourth current applications is sensed, determine a first nerve proximity state is present;
   (d) when the first evoked response is sensed, non-simultaneously titrate additional first current to the first electrode and additional second current to the second electrode and sense additional evoked responses, when they are produced, until an evoked response is sensed for only one of the first and second electrodes in response to equal amplitudes of current application;
   (e) after step (d), simultaneously communicate a supplemental first current application to the first electrode, a supplemental second current application to the second electrode, a supplemental third current application to the third electrode, and a supplemental fourth current application to the fourth electrode;
   (f) sense a supplemental first evoked response to any of the supplemental first, second, third, and fourth current applications when the supplemental first evoked response occurs;
   (g) when no evoked response to the supplemental first, second, third, and fourth current applications is sensed, determine the first nerve proximity state is present;
   (h) when the supplemental first evoked response is sensed, non-simultaneously titrate additional third current to the third electrode and additional fourth current to the fourth electrode and sense supplemental evoked responses until a supplemental evoked response is sensed for only one of the third and fourth electrodes in response to equal amplitudes of current application;
   (i) communicate to a user of the surgical instrument a second nerve proximity state is present indicating a nerve is closer to one of the first, second, third, and fourth electrodes than another of the first, second, third, and fourth electrodes in response to at least one of steps (d) and (h);

wherein titrating the additional first, second, third, and fourth currents includes incrementally changing the additional first, second, third, and fourth currents.

2. The system of claim 1, wherein the memory includes at least one memory and the processor includes at least one processor.

3. The system of claim 2, wherein the processor is configured to cause the current source unit to, when the first evoked response is sensed, titrate additional first current to the first electrode and additional second current to the second electrode, without supplying additional current to the third and fourth electrodes, and sense additional evoked responses when they are produced, until an evoked response is sensed for only one of the first and second electrodes in response to equal amplitudes of current application.

4. The system of claim 3 wherein the surgical instrument includes at least one of a probe, a dilator, a retractor, snips, a cutting device, a rasp, a trocar, spreaders, distracters, a shim, a scraper, a chisel, disc cutters, a curette, a suction probe, or tamps.

5. The system of claim 4 comprising the current source unit, which includes a current source, an amplifier, a filter, an A/D converter, a D/A converter, and a multiprocessor system, wherein the multiprocessor system includes the memory and the processor.

6. An article comprising a non-transitory medium storing instructions that enable a processor-based system to:
(a) simultaneously communicate, via a current source unit, a first current application to a first electrode, a second current application to a second electrode, a third current application to a third electrode, and a fourth current application to a fourth electrode when the first, second, third, and fourth electrodes are coupled to a surgical instrument;
(b) sense a first evoked response to any of the first, second, third, and fourth current applications when the first evoked response occurs;
(c) when no evoked response to the first, second, third, and fourth current applications is sensed, determine a first nerve proximity state is present;
(d) when the first evoked response is sensed, non-simultaneously titrate additional first current to the first electrode and additional second current to the second electrode and sense additional evoked responses until an evoked response is sensed for only one of the first and second electrodes in response to equal amplitudes of current application;
(e) after step (d), simultaneously communicate a supplemental first current application to the first electrode, a supplemental second current application to the second electrode, a supplemental third current application to the third electrode, and a supplemental fourth current application to the fourth electrode;
(f) sense a supplemental first evoked response to any of the supplemental first, second, third, and fourth current applications when the supplemental first evoked response occurs;
(g) when no evoked response to the supplemental first, second, third, and fourth current is sensed, determine the first nerve proximity state is present;
(h) when the supplemental first evoked response is sensed, non-simultaneously titrate additional third current to the third electrode and additional fourth current to the fourth electrode and sense supplemental evoked responses until a supplemental evoked response is sensed for only one of the third and fourth electrodes in response to equal amplitudes of current application;
(i) communicate to a user of the surgical instrument a second nerve proximity state is present indicating a nerve is closer to one of the first, second, third, and fourth electrodes than another of the first, second, third, and fourth electrodes in response to at least one of steps (d) and (h);
wherein titrating the additional first, second, third, and fourth currents includes incrementally changing the additional first, second, third, and fourth currents.

7. The article of claim 6 storing instructions that enable the system to:
simultaneously communicate current to the first and second electrodes while communicating no current to the third and fourth electrodes;
sense an evoked response to the simultaneously communicated current when the evoked response occurs;
when no evoked response to the simultaneously communicated current is sensed, simultaneously communicate current to the third and fourth electrodes while communicating no current to the first and second electrodes.

8. The article of claim 7, wherein communicating the first current application to the first electrode comprises communicating bipolar current between the first electrode and a reference electrode.

9. The article of claim 8, wherein the first, second, third, fourth, and reference electrodes are all included on a distal end portion of the surgical instrument.

10. The article of claim 9, wherein the surgical instrument includes at least one of a probe, a dilator, a retractor, snips, a cutting device, a rasp, a trocar, spreaders, distracters, a shim, a scraper, a chisel, disc cutters, a curette, a suction probe, or tamps.

11. An article comprising a non-transitory medium storing instructions that enable a processor-based system to:
(a) communicate, via a current source unit, a first current application to a first electrode, a second current application to a second electrode, a third current application to a third electrode, and a fourth current application to a fourth electrode when the first, second, third, and fourth electrodes are coupled to a surgical instrument;
(b) sense a first evoked response to any of the first, second, third, and fourth current applications when the first evoked response occurs;
(c) when no evoked response to the first, second, third, and fourth current applications is sensed, determine a first nerve proximity state is present;
(d) when the first evoked response is sensed, non-simultaneously titrate additional first current to the first electrode and additional second current to the second electrode and sense additional evoked responses until an evoked response is sensed for only one of the first and second electrodes in response to equal amplitudes of current application;
(e) communicate to a user of the surgical instrument a second nerve proximity state is present indicating a nerve is closer to one of the first, second, third, and fourth electrodes than another of the first, second, third, and fourth electrodes in response to step (d);
wherein titrating the additional first and second currents includes incrementally changing the additional first and second currents.

12. The article of claim 11 storing instructions that enable the system to:
communicate current to the first and second electrodes while communicating no current to the third and fourth electrodes;

sense an evoked response to the communicated current when the evoked response occurs;

when no evoked response to the communicated current is sensed, communicate current to the third and fourth electrodes while communicating no current to the first and second electrodes.

13. The article of claim 11 storing instructions that enable the system to simultaneously communicate, via the current source unit, the first current application to the first electrode, the second current application to the second electrode, the third current application to the third electrode, and the fourth current application to the fourth electrode when the first, second, third, and fourth electrodes are coupled to a surgical instrument.

14. The article of claim 13 storing instructions that enable the system to:

simultaneously communicate current to the first and second electrodes while communicating no current to the third and fourth electrodes;

sense an evoked response to the simultaneously communicated current when the evoked response occurs;

when no evoked response to the simultaneously communicated current is sensed, simultaneously communicate current to the third and fourth electrodes while communicating no current to the first and second electrodes.

15. The article of claim 14, wherein communicating the first current application to the first electrode comprises communicating bipolar current between the first electrode and a reference electrode.

16. The article of claim 15, wherein the first, second, third, fourth, and reference electrodes are all included on a distal end portion of the surgical instrument.

17. The article of claim 16, wherein the surgical instrument includes at least one of a probe, a dilator, a retractor, snips, a cutting device, a rasp, a trocar, spreaders, distracters, a shim, a scraper, a chisel, disc cutters, a curette, a suction probe, or tamps.

* * * * *